US011883540B2

(12) United States Patent
Hoare et al.

(10) Patent No.: US 11,883,540 B2
(45) Date of Patent: Jan. 30, 2024

(54) STIMULUS ACTIVATED CORK-SHELL CAPSULES

(71) Applicant: McMaster University, Hamilton (CA)

(72) Inventors: Todd Hoare, Ancaster (CA); Jonathan Dorogin, Richmond Hill (CA); David Koff, Ancaster (CA); Andrew Singh, Toronto (CA)

(73) Assignee: McMaster University, Hamilton (CA)

( * ) Notice: Subject to any disclaimer, the term of this patent is extended or adjusted under 35 U.S.C. 154(b) by 1 day.

(21) Appl. No.: 17/320,446

(22) Filed: May 14, 2021

(65) Prior Publication Data

US 2021/0353550 A1 Nov. 18, 2021

Related U.S. Application Data

(60) Provisional application No. 63/025,553, filed on May 15, 2020.

(51) Int. Cl.
*A61K 9/50* (2006.01)
*A61K 9/00* (2006.01)

(52) U.S. Cl.
CPC .......... *A61K 9/5031* (2013.01); *A61K 9/0009* (2013.01); *A61K 9/501* (2013.01)

(58) Field of Classification Search
CPC .... A61K 9/5031; A61K 9/0009; A61K 9/501; A61K 9/1611; A61K 9/1641; A61K 9/08
See application file for complete search history.

(56) References Cited

PUBLICATIONS

Néstor et al., Ultrasonics 51 (2011) 839-845. (Year: 2011).*
Zhang et al., ACS Appl. Mater. Interfaces 2017, 9, 21475-21495. (Year: 2017).*
Yuan et al. (2015) PLoS One 10(7): e0132609. doi:10.1371/journal.pone.0132609. (Year: 2015).*
Dorogin, (2019) http://hdl.handle.net/11375/23799, McMaster University_ Biomedical Engineering Thesis (Year: 2019).*
Caruso, M.M., et al., Mechanically-induced chemical changes in polymeric materials. Chem Rev, 2009. 109(11): p. 5755-98.
Coussios, C.C. and R.A. Roy, Applications of Acoustics and Cavitation to Noninvasive Therapy and Drug Delivery. Annu Rev Fluid Mech, 2008. 40(1): p. 395-420.
Escoffre, J.M., et al., Doxorubicin delivery into tumor cells with ultrasound and microbubbles. Mol Pharm, 2011. 8(3): p. 799-806.
Liu, J., et al., pH-sensitive nano-systems for drug delivery in cancer therapy. Biotechnol Adv, 2014. 32(4): p. 693-710.
Li, J., C. Nagamani, and J.S. Moore, Polymer mechanochemistry: from destructive to productive. Acc Chem Res, 2015. 48(8): p. 2181-90.
Choi, S.W., Y. Zhang, and Y. Xia, A temperature-sensitive drug release system based on phase-change materials. Angew Chem Int Ed Engl, 2010. 49(43): p. 7904-8.
Hoare, T. and R. Pelton, Highly pH and Temperature Responsive Microgels Functionalized with Vinylacetic Acid. Macromolecules, 2004. 37(7): p. 2544-2550.
Li, W., et al., Gold nanocages covered with thermally-responsive polymers for controlled release by high-intensity focused ultrasound. Nanoscale, 2011. 3(4): p. 1724-30.
Liu, H., et al., Hydrophobic interaction-mediated capture and release of cancer cells on thermoresponsive nanostructured surfaces. Adv Mater, 2013. 25(6): p. 922-7.
Ta, T. and T.M. Porter, Thermosensitive liposomes for localized delivery and triggered release of chemotherapy. J Control Release, 2013. 169(1-2): p. 112-25.
Tan, H., et al., Thermosensitive injectable hyaluronic acid hydrogel for adipose tissue engineering. Biomaterials, 2009. 30(36): p. 6844-53.
Cheng, W., et al., pH-Sensitive Delivery Vehicle Based on Folic Acid-Conjugated Polydopamine-Modified Mesoporous Silica Nanoparticles for Targeted Cancer Therapy. ACS Appl Mater Interfaces, 2017. 9(22): p. 18462-18473.
Felber, A.E., M.H. Dufresne, and J.C. Leroux, pH-sensitive vesicles, polymeric micelles, and nanospheres prepared with polycarboxylates. Adv Drug Deliv Rev, 2012. 64(11): p. 979-92.
Li, H.J., et al., Smart Superstructures with Ultrahigh pH-Sensitivity for Targeting Acidic Tumor Microenvironment: Instantaneous Size Switching and Improved Tumor Penetration. ACS Nano, 2016. 10(7): p. 6753-61.
Hu, J., G. Zhang, and S. Liu, Enzyme-responsive polymeric assemblies, nanoparticles and hydrogels. Chem Soc Rev, 2012. 41(18): p. 5933-49.
Li, Y., et al., Enzyme-Responsive Polymeric Vesicles for Bacterial-Strain-Selective Delivery of Antimicrobial Agents. Angew Chem Int Ed Engl, 2016. 55(5): p. 1760-4.
Muanprasat, C. and V. Chatsudthipong, Chitosan oligosaccharide: Biological activities and potential therapeutic applications. Pharmacol Ther, 2017. 170: p. 80-97.
Napoli, A., et al., Glucose-oxidase Based Self-Destructing Polymeric Vesicles. Langmuir, 2004. 20(9): p. 3487-3491.
Yu, J., et al., Stimuli-Responsive Delivery of Therapeutics for Diabetes Treatment. Bioeng Transl Med, 2016. 1(3): p. 323-337.

(Continued)

*Primary Examiner* — Robert S Cabral
(74) *Attorney, Agent, or Firm* — BERESKIN & PARR LLP/S.E.N.C.R.L., s.r.l.; Michael Fenwick (57) ABSTRACT

The present application relates to a vehicle whose shell material is modified with at least one additional secondary phase that acts as a cork. In the presence of an energy source (preferably ultrasound), the corks embedded in the shell are either removed from the shell to create permanent pores or perturbed within the shell to create transient pores that can control transport in or out of the vehicle.

23 Claims, 7 Drawing Sheets

(56) References Cited

PUBLICATIONS

Di, J., et al., Ultrasound-triggered noninvasive regulation of blood glucose levels using microgels integrated with insulin nanocapsules. Nano Research, 2017. 10(4): p. 1393-1402.

Song, G., et al., Perfluorocarbon-Loaded Hollow Bi2Se3 Nanoparticles for Timely Supply of Oxygen under Near-Infrared Light to Enhance the Radiotherapy of Cancer. Adv Mater, 2016. 28(14): p. 2716-23.

Volodkin, D.V., A.G. Skirtach, and H. Mohwald, Near-IR remote release from assemblies of liposomes and nanoparticles. Angew Chem Int Ed Engl, 2009. 48(10): p. 1807-9.

Xu, J.S., et al., Synthesizing and binding dual-mode poly (lactic-co-glycolic acid) (PLGA) nanobubbles for cancer targeting and imaging. Biomaterials, 2010. 31(7): p. 1716-22.

Brazel, C.S., Magnetothermally-responsive nanomaterials: combining magnetic nanostructures and thermally-sensitive polymers for triggered drug release. Pharm Res, 2009. 26(3): p. 644-56.

Ulbrich, K., et al., Targeted Drug Delivery with Polymers and Magnetic Nanoparticles: Covalent and Noncovalent Approaches, Release Control, and Clinical Studies. Chem Rev, 2016. 116(9): p. 5338-431.

Zhang, Y., et al., Mechanical Force-Triggered Drug Delivery. Chem Rev, 2016. 116(19): p. 12536-12563.

Figueiredo, M. and R. Esenaliev, PLGA Nanoparticles for Ultrasound-Mediated Gene Delivery to Solid Tumors. J Drug Deliv, 2012. 2012: p. 767839.

Hernot, S. and A.L. Klibanov, Microbubbles in ultrasound-triggered drug and gene delivery. Adv Drug Deliv Rev, 2008. 60(10): p. 1153-66.

Li, P., et al., Ultrasound triggered drug release from 10-hydroxycamptothecin-loaded phospholipid microbubbles for targeted tumor therapy in mice. J Control Release, 2012. 162(2): p. 349-54.

Deckers, R., et al., New insights into the HIFU-triggered release from polymeric micelles. Langmuir, 2013. 29(30): p. 9483-90.

Prince, J.L. and J.M. Links, Medical Imaging Signals and Systems, in Medical Imaging Signals and Systems. 2006, Pearson Prentice Hall.

Moyer, L.C., et al., High-intensity focused ultrasound ablation enhancement in vivo via phase-shift nanodroplets compared to microbubbles. J Ther Ultrasound, 2015. 3: p. 7.

Liu, Y., H. Miyoshi, and M. Nakamura, Encapsulated ultrasound microbubbles: therapeutic application in drug/gene delivery. J Control Release, 2006. 114(1): p. 89-99.

Villanueva, F.S., Ultrasound mediated destruction of DNA-loaded microbubbles for enhancement of cell-based therapies: new promise amidst a confluence of uncertainties? JACC Cardiovasc Imaging, 2009. 2(7): p. 880-2.

Fong, W.K., et al., Responsive self-assembled nanostructured lipid systems for drug delivery and diagnostics. J Colloid Interface Sci, 2016. 484: p. 320-339.

Kang, M., G. Huang, and C. Leal, Role of lipid polymorphism in acoustically sensitive liposomes. Soft Matter, 2014. 10(44): p. 8846-54.

Schroeder, A., et al., Controlling Liposomal Drug Release with Low Frequency Ultrasound: Mechanism and Feasibility. Langmuir, 2007. 23(7): p. 4019-4025.

Tang, J., et al., Controlled drug release from ultrasound-visualized elastic eccentric microcapsules using different resonant modes. J Mater Chem B, 2018. 6(13): p. 1920-1929.

Swider, E., et al., Customizing poly(lactic-co-glycolic acid) particles for biomedical applications. Acta Biomater, 2018. 73: p. 38-51.

Ahmad, Z., et al., Generation of multilayered structures for biomedical applications using a novel tri-needle coaxial device and electrohydrodynamic flow. J R Soc Interface, 2008. 5(27): p. 1255-61.

Gao, Y., et al., Optimising the shell thickness-to-radius ratio for the fabrication of oil-encapsulated polymeric microspheres. Chem Eng J, 2016. 284: p. 963-971.

Jaworek, A. and A.T. Sobczyk, Electrospraying route to nanotechnology: An overview. J Electrostat, 2008. 66(3-4): p. 197-219.

Li, Z. and C. Wang, Effects of Working Parameters on Electrospinning, in One-Dimensional nanostructures. 2013. p. 15-28.

Moghaddam, M.K., S.M. Mortazavi, and T. Khaymian, Micro/nano-encapsulation of a phase change material by coaxial electrospray method. Iran Polym J, 2015. 24(9): p. 759-774.

Smallwood, I.M., Handbook of Organic Solvent Properties. 1996, New York: Halsted Press.

Xu, Y. and M.A. Hanna, Electrospray encapsulation of water-soluble protein with polylactide. Effects of formulations on morphology, encapsulation efficiency and release profile of particles. Int J Pharm, 2006. 320(1-2): p. 30-6.

Wu, F., et al., Grafting polymerization of polylactic acid on the surface of nano-SiO2 and properties of PLA/PLA-grafted-SiO2nanocomposites. J Appl Polym Sci, 2013. 129(5): p. 3019-3027.

Lee, Y.-C., et al., Optical Properties of Fluorescein labeled Organoclay. Photochem Photobiol, 2010. 86(3): p. 520-527.

* cited by examiner

STIMULUS ACTIVATED CORK-SHELL CAPSULES

CROSS-REFERENCE TO RELATED APPLICATIONS

The present application claims the benefit of priority from U.S. provisional application No. 63/025,553 filed on May 15, 2020, the contents of which are incorporated herein by reference in their entirety.

FIELD

The present application relates to a cork-shell particle capsule comprising a polymeric continuous outer shell phase and a releasable cork phase embedded within the outer shell phase, wherein the cork is released upon an external stimulus.

BACKGROUND

Controlled drug delivery has many potential benefits in medicine. "On-demand" or pulsatile delivery vehicles offer particular advantages in terms of being able to dose a drug at a particular time and/or with a particular rate in response to either the microenvironment of the delivery vehicle or an external stimulus [1-5].

On-demand drug delivery systems have been designed by applying many different methods of activation, including both internal microenvironments or external stimuli. Those systems relying on internal microenvironments are identified as passive delivery systems and are stimulated primarily by endogenous changes to temperature [6-11], pH [4, 12-14], enzymatic activity [15-17] or local chemical gradients [18-20] (among other factors) to release their contents. Those systems relying on external stimuli can be activated by various types of irradiation [21-23], magnetic fields [1, 24-26], or ultrasound signals [20, 27-29]. Ultrasound triggered drug delivery has attracted particular interest due to its release mechanism being related to mechanical agitation (inducing vibrations on a material at frequencies higher than 20 kHz [10, 30, 31]) and/or the creation of pressure gradients (via cavitation) within generic materials as opposed to chemical reactions and/or physical stimuli (e.g. heat, pH, or magnetic fields) that require the use of specific materials for function.

Release of payloads in ultrasound triggered drug delivery can be mediated by continuous wave or pulsed wave activation [2, 30]. For continuous wave activation, the target is exposed to a constant ultrasound signal which in turn begins to heat the target and its surroundings, causing the target to melt and/or deform to become more permeable [10]. Continuous wave activation is generally not used clinically because the heat generation has the potential to burn the subject [32]. For pulsed wave activation, the target is exposed to periodic ultrasound signal that creates shear which in turn causes the target to rupture and release its payload [27, 28, 33, 34]. Pulsed wave activation is difficult to implement practically because, once the target ruptures, dosing controls can become problematic. However, with the correct material, pulsed ultrasound wave activation can mediate the transport of a payload through the shell of the target [20, 35-38]. The challenge is the necessity to continuously expose the target to pulsed waves to facilitate release, restricting the clinical applicability of such systems; in addition, the shear tension and stress applied during activation may damage cells surrounding the target [30].

On this basis, the development of a delivery vehicle that is able to overcome the issues associated with existing "on-demand" drug delivery vehicles—in particular a vehicle that can be fabricated from non-specific materials, enable activation using widely-available medical infrastructure, respond in a metered way to external stimuli for properly regulated dose control, and release its payload without burning the subject or damaging extensively the healthy cells surrounding the vehicle—would be highly beneficial for clinically enabling on-demand drug delivery.

SUMMARY

The present application relates to microcapsule formulations that can entrap a payload and release that payload and/or expose the external environment to the payload upon the application of an ultrasound signal. In particular, the present application relates to a cork-shell particle capsule comprising a polymeric continuous outer shell phase and a releasable cork phase embedded within the outer shell phase, wherein the cork phase is released upon a stimulus.

Accordingly, in one embodiment, the present disclosure is directed to a cork-shell particle, comprising:
a) a continuous outer shell phase comprising at least one first polymer; and
b) a releasable cork phase embedded and/or dispersed within the outer shell phase, wherein the cork phase is perturbed within the outer shell phase upon exposure to an external stimulus.

In one embodiment, the cork phase is irreversibly released from the outer shell to create a pore within the outer shell.

In another embodiment, the cork phase is transiently perturbed within the outer shell to create a pore within the outer shell.

In another embodiment, the external stimulus is ultrasound energy.

In another embodiment, the cork phase comprises an inorganic oxide covalently linked to a second polymer.

The present application further describes the fabrication and guidelines for use of a hollow particulate device (the vehicle, or the cork-shell particle) in which one or more secondary material(s) (the cork(s), which may or may not be chemically distinct from the shell material) are embedded in the shell of the vehicle. In such a composition, one or more of the following attributes may be leveraged in an application depending on the nature of the shell and cork(s): (1) the dissociation of the cork phase from the shell phase following the application of an internal or external energy source to lead to the formation of pores in the retained shell phase(s); (2) the use of ultrasound or another energy source to vibrate the cork phase within the continuous shell phase, creating dynamic pores at the cork-shell interface that can facilitate transport in or out of the capsule; (3) the filling and/or emptying of the vehicle in a controlled manner through the pores generated upon activation; (4) the imaging of either the cork phase or the shell phase.

Controlling the dosage of drugs using ultrasound triggered drug delivery is difficult due to the mechanism by which ultrasound triggered drug delivery occurs. Release occurs either through the breaking of the shell of the delivery vehicle (herein named Ultrasound Triggered Microbubble Destruction, or UTMD) or through continuous ablation by ultrasound signals that instigate diffusion through the shell material (herein named Ultrasound Mediated Shell Diffusion, or UMSD). In an embodiment of the application, a delivery vehicle containing multiple phases in the shell is used to overcome the difficulties of controlling dosage associated with UTMD and the necessity of continuous ultrasound application for release associated with UMSD. The drug delivery vehicle comprises (1) an encapsulated phase (the core, core phase, or inner core), which in an embodiment is an aqueous phase dissolving or suspending a drug, a fluorescent label, a radiolabel, a biomarker, or formulations thereof (henceforth referred to as the payload), and (2) a shell phase containing at least one material not miscible with the inner aqueous phase and at least one additional material dispersed or embedded within the shell phase (the cork). The combination of the inner phase and the shell phase with or without the corks is henceforth referred to as the capsule. Upon exposure to an ultrasound signal or another suitable energy source, the cork material is either released from the shell or vibrated within the shell without substantially disrupting the integrity of the capsule, creating a pore that may be permanent (if the cork is popped out) or dynamic (if the cork remains in the shell) that allows for diffusion both in and out of the delivery vehicle. Longer exposure times and/or higher energy applications would release more corks from the capsule (thus creating more pores) or, in an embodiment, maintain the dynamic pores created by the vibration of the corks within the shell for a longer period of time, allowing control over the rate of emptying of the contents of the inner core to the surroundings and/or entry of materials in the vehicle environment into the inner core.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings.

DETAILED DESCRIPTION

Definitions

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise.

In embodiments comprising an "additional" or "second" component, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "suitable" as used herein means that the selection of the particular compound or conditions would depend on the type and purpose of the specific synthetic manipulation to be performed and the identity of the molecule(s) to be transformed as per the knowledge of one skilled in the art, including all relevant reaction conditions such as solvent, reaction time, reaction temperature, reaction pressure, reactant ratio, and requirement for inert environment reactions.

The term "w/w" as used herein means the number of grams of solute in 100 g of solution.

The term "w/v" as used herein refers to the number of grams of solution in 100 mL of solvent.

The term "cork-shell" as used herein refers to, for example, a particle which is defined by an outer shell polymeric shell in which a cork phase is embedded or dispersed within, or otherwise interspersed throughout the outer shell, and which upon exposure to a stimulus, the cork phase is released from the shell to form a pore.

The term "outer shell" as used herein refers to a closed polymeric shell or outer membrane or wall which defines an inner core which can hold one or more materials.

The term "releasable cork phase" as used herein refers to a phase which is embedded or dispersed within, or otherwise interspersed throughout the outer shell, such that upon exposure to a stimulus, the cork phase is perturbed within the outer shell to form a pore within the outer shell.

The term "external stimulus" as used herein refers to a stimulus which perturbs the cork phase within the outer shell such that the cork phase is perturbed within the outer shell to create a pore within the shell phase.

DETAILED DESCRIPTION

The present application relates to capsule-based formulations that can entrap a payload and release that payload and/or expose the external environment to the payload upon the application of an ultrasound signal. In particular, the present application relates to a cork-shell particle capsule comprising a polymeric continuous outer shell phase and a releasable cork phase embedded within the outer shell phase, wherein the cork phase is perturbed within the shell upon the application of a stimulus.

In one embodiment, the disclosure is directed to a vehicle comprising:
  an inner core phase containing one or more payload materials and;
  an outer phase comprising a continuous primary phase embedded with one or more secondary phases;
    wherein a stimulus may remove or perturb at least one of the secondary phases in the outer phase without significantly disrupting the continuous primary phase and thus enable control over diffusion through the outer phase.

In one embodiment, the vehicle is a microparticle or a nanoparticle.

In another embodiment, the inner core phase comprises any combination of payload materials that may be dissolved or dispersed inside the core.

In a further embodiment, the one or more of the payload materials comprises a biologically active entity, inorganic material, or combinations thereof.

In another embodiment, the biologically active entity is a drug, a protein, an antibody, an enzyme, a polynucleotide, or a particulate formulation thereof.

In a further embodiment, the particulate formulation is a nanoparticle, a nanogel, a liposome, a polymersome, a micelle, a dendrimer, a conjugate, and/or another type of carrier.

In a further embodiment, the inorganic material is a salt, a metal, a ceramic, an imaging agent, or a nanoparticulate formulation thereof.

In another embodiment, the combination of the biologically active entity and inorganic material is an organometallic compound.

In a further embodiment, the vehicle is applied to the formulation and/or delivery of therapeutics for human, animal, plant, micro-organism, or other types of use.

In another embodiment, one or more of the materials contained within the inner core phase can be used for sensing applications.

In a further embodiment, the material used for sensing is an enzyme, a polynucleotide, a fluorescent probe, a radioactive probe, a heavy metal, a phosphorescent probe, a magnetically active probe, and/or another type of probe useful for biological imaging and/or chemical analysis.

In a further embodiment, the outer phase comprises a continuous shell material and at least one dispersed material.

In another embodiment, the continuous shell material is a polymer. In one embodiment, the continuous shell comprises one or more different polymers.

In a further embodiment, the polymer is a polyester, a polyurethane, a poly(meth)acrylate, a poly(amino ester), a polyurea, a polyolefin, or copolymers thereof. In another embodiment, the polyester is poly(lactic acid), poly(glycolic acid), copolymers of lactic and glycolic acid, polycaprolactone, poly(valerolactone), poly(hydroxy valerate), poly(ethylene succinate), poly(ε-decalactone), poly(4-hydroxybutyrate), poly(para-dioxanone), poly(beta-malic acid), or copolymers thereof.

In a further embodiment, the secondary phase comprises a material that may or may not be chemically distinct from the continuous primary phase.

In another embodiment, the secondary phase comprises an inorganic oxide including (but not limited to) silicon dioxide, sodium oxide, calcium oxide, potassium oxide, barium oxide, mesoporous silica, or other metal oxides, a metal salt, a polymer that may or may not be chemically distinct from the continuous primary phase, an organometallic compound, or a contrast agent.

In a further embodiment, one or both of the inner or outer core phases further contains a surfactant.

In another embodiment, the vehicle is formed via any suitable fabrication method including single emulsion-solvent evaporation, double emulsion-solvent evaporation, spray-drying, interfacial microprecipitation or nanoprecipitation, microfluidics, electro-atomization, or membrane extrusion microemulsification.

In a further embodiment, the vehicle is formed via electro-atomization.

In a further embodiment, the removal or perturbation of one or more of the secondary phases occurs upon application of a stimulus including ultrasound, magnetic fields, irradiation, pH changes, temperature changes, or enzymatic activity.

In a further embodiment, the removal or perturbation of one or more of the secondary phases occurs through ultrasound activation.

In one embodiment, the ultrasound activation removes one or more secondary phases in the outer phase.

In a further embodiment, one or more secondary phases are perturbed within the outer phase to create pores only during ultrasound activation.

In a further embodiment, duration, pressure, power, or frequency of ultrasound affects one or more of the following:
  number of pores created by the removal of one or more of the secondary phases from the outer phase;
  free volume created by the transient perturbation of one or more of the secondary phases within the outer phase;
  rate at which the contents of the inner core of the vehicle may be emptied; and/or
  rate at which the inner core of the vehicle may be filled.

In a further embodiment, the number of pores and/or free volume created by the application of ultrasound is controlled by any combination of duration, pressure, power and/or frequency of the ultrasound.

In one embodiment, emptying and/or filling the contents of the inner core are controlled by any combination of duration, pressure, power and/or frequency of the ultrasound.

In an embodiment of the application, the delivery vehicle is fabricated by traditional methods known to the art, including but not limited to single emulsion-solvent evaporation, double emulsion-solvent evaporation, spray-drying, interfacial microprecipitation or nanoprecipitation, microfluidics, electro-atomization, or membrane extrusion microemulsification [39]. In an embodiment of the application, the delivery vehicle is fabricated using a combination of interfacial microprecipitation and electro-atomization, herein named immersion coaxial electrospraying (ImCES) or electrically-assisted interfacial precipitation (EAIP).

In an embodiment, an inner phase containing the payload and surfactant(s) is co-extruded with a shell phase containing all necessary materials to form both the shell (i.e. both the continuous shell phase and the cork(s)) into a bath that contains one or more surfactant(s) to stabilize the particles. The size of the inner core and the thickness of the capsule may be controlled by the volumes/flow rates of the core and shell phases, the concentrations of surfactant(s) in the core and continuous phases, the concentration of the dissolved material(s) in the core and shell phases, the type of solvent (s) used in the core and shell phases, the voltage applied, and the stirring speed of the collector [40-46]. In an embodiment, an aqueous inner phase in which a payload and surfactant(s) are dissolved, an organic solvent in which the shell material(s) are dissolved and the cork materials are dispersed, and an aqueous continuous phase in which surfactant(s) are dissolved are used.

In an embodiment, the aqueous inner phase contains some concentration of surfactants and/or surface-active agents such as (but not limited to) Tween® 80, Tergitol™ NP-4, or albumin (BSA) and some concentration of a payload(s) including (but not limited to) fluorescent label(s), protein(s), metal ion(s), contrast agent(s), drug(s), molecular affinity agent(s) (including enzymes, polynucleotides such as DNA/RNA, antibodies, or other such agents), and/or nanoscale or microscale formulations thereof. In the same embodiment, the shell phase contains some concentration of a capsule-forming polymer including (but not limited to) poly(lactide-co-glycolide) (PLGA), poly lactide, poly glycolide, polydimethylsiloxane, polystyrene, polycaprolactone, polyesters, polyurethanes, polycarbonates, polyanhydrides, or copolymers thereof dissolved in an appropriate organic solvent facilitating the solubility of the capsule polymer as well as some concentration of a cork material suspended in, but not soluble or not yet dissolved, in that same solvent. In an embodiment, the cork material is an inorganic oxide including (but not limited to) silicon dioxide, sodium oxide, calcium oxide, potassium oxide, barium oxide, mesoporous silica, or other metal oxides, metal salts, polymers which may or may not be chemically distinct from the shell phase, organometallic compounds, or some contrast agent. In an embodiment, the cork materials are surface functionalized with the capsule material to promote good dispersion in the shell. In the same embodiment, a continuous outer water phase containing some concentration of surfactants or surface-active polymers including (but not limited to) polyvinyl alcohol (henceforth referred as PVA) or Span® 80 is chosen.

In an aspect of the application, the corks may be released from or vibrated within the delivery vehicle by any internal or external stimulus, including but not limited to ultrasound, magnetic fields, irradiation, pH changes, temperature changes, or enzymatic activity. In an embodiment, the stimulus is ultrasound. In such an embodiment, ultrasound of a relevant frequency, acoustic pressure, ultrasound power, pulse repetition frequency, voltage, duration, proximity, or any additional manipulated variable is used to drive the release or vibration of the corks in the shell of the capsule, creating a pore or multiple pores in the shell. In a further embodiment, the formation of pores can be adjusted to control the release rate of the payload or in-diffusion of analytes, substrates, or other relevant chemicals into the vehicle.

The present disclosure also includes a cork-shell particle comprising a) a continuous outer shell phase comprising at least one first polymer; and
b) a releasable cork phase embedded and/or dispersed within the outer shell phase, wherein the cork phase is perturbed within the outer shell phase upon exposure to an external stimulus.

In one embodiment, the cork phase is irreversibly released from the outer shell to create a pore within the outer shell.

In another embodiment, the cork phase is transiently perturbed within the outer shell to create a pore within the outer shell.

In another embodiment, upon exposure to ultrasound energy, the cork phase has a different mechanical index from the continuous outer shell phase, such that the cork phase is irreversibly or transiently released from or vibrated independently within the outer shell phase to create a pore (permanent or temporary).

In one embodiment, the cork phase is irreversibly or transiently released from or vibrated within the delivery vehicle by any internal or external stimulus, such as an external energy source, including but not limited to ultrasound, magnetic fields, irradiation, pH changes, temperature changes, or enzymatic activity.

In another embodiment, the cork phase is a particulate phase physically embedded in the outer shell phase, wherein the properties of the cork phase are manipulated by an external stimulus. In one embodiment, upon exposure to ultrasound energy, the cork phase is irreversibly released from the outer shell. In another embodiment, the cork phase is vibrated within the outer shell.

In another embodiment, the outer shell phase is prepared in a solvent and the cork phase is insoluble in the solvent, such that the cork phase becomes embedded, dispersed and/or otherwise interspersed within the outer shell phase. In one embodiment, the solvent is a halogenated solvent such as dichloromethane.

In an embodiment, the outer shell phase is dissolved in an organic solvent and the inner phase is dissolved in water. In one embodiment, the outer shell phase and the inner core are immiscible.

In another embodiment, the external stimulus is ultrasound energy.

In another embodiment, the cork phase is an inorganic oxide.

In another embodiment, the cork phase comprises an inorganic oxide covalently linked to a second polymer.

In another embodiment, the polymer of the shell phase is a polyester, a polyurethane, a poly(meth)acrylate, a poly (amino ester), a polyurea, a polyolefin, a polyanhydride, or copolymers thereof.

In a further embodiment, at least one polymer of the shell phase is a polyester. In another embodiment, the first polymer is poly(lactic acid), poly(glycolic acid), copolymers of lactic and glycolic acid, polycaprolactone, poly(valerolactone), poly(hydroxy valerate), poly(ethylene succinate), poly(ε-decalactone), poly(4-hydroxybutyrate), poly(para-dioxanone), or poly(beta-malic acid).

In another embodiment, the polyester is poly(lactic acid-co-glycolic acid).

In a further embodiment, the poly(lactic acid-co-glycolic acid) has the formula wherein m and n are integers from 1 to 10,000 and the ratio between m and n can be any number. In one embodiment, the integers m and are between about 1-2000, or about 500-1500.

In an embodiment, the ratio between m and n is about 65:35, or about 50:50, or about 35:65.

In an embodiment, the total molecular weight of the polymer is about 5,000, or about 40,000, or about 75,000. In one embodiment, the molecular weight of the polymer is between about 5,000 to about 75,000.

In one embodiment, the size of the capsules is between about 1-100, about 1-50, or about 2-10 microns.

In another embodiment, the inorganic oxide is silicon dioxide, sodium oxide, calcium oxide, potassium oxide, barium oxide, or mesoporous silica, or mixtures thereof.

In a further embodiment, the inorganic oxide is silicon dioxide. In one embodiment, the inorganic oxide is silicon dioxide beads.

In another embodiment, the silicon dioxide is covalently linked to the second polymer with an amine linker.

In another embodiment, the amine linker is 3-aminopropyltriethoxysilane, other amino-containing silicones, or an amine-containing heterobifunctional crosslinker with hydroxyl group reactivity.

In another embodiment, the second polymer is a polyester such as polylactide, polyglycolide, poly(lactide-co-glycolide) copolymers, polycaprolactone, poly(valerolactone), poly(hydroxy valerate), poly(ethylene succinate), poly(ε-decalactone), poly(4-hydroxybutyrate), poly(para-dioxanone), poly(beta-malic acid). In another embodiment, the second polymer is a polyurethane, a poly(meth)acrylate, a poly(amino ester), a polyanhydride, a polyurea, a polyolefin, or copolymers thereof.

In another embodiment, the polyester is poly(lactic acid-co-glycolic acid).

In another embodiment, the second polymer has the formula wherein m and n are integers from 1 to 10,000. In one embodiment, the integers m and are between about 1-2000, or about 500-1500.

In an embodiment, the ratio between m and n is about 65:35, or about 50:50, or about 35:65.

In an embodiment, the total molecular weight of the polymer is about 5,000, or about 40,000, or about 75,000. In one embodiment, the molecular weight of the polymer is between about 5,000 to about 75,000.

In another embodiment, the cork-phase has the following formula

In another embodiment, the first and second polymer are the same.

In another embodiment, the cork phase releases from the outer shell phase to create a pore within the outer shell phase upon exposure to a stimulus.

In another embodiment, the particle is a microparticle or a nanoparticle.

In a further embodiment, the continuous outer shell phase defines an inner core phase comprising one or more entities which are released from the inner core phase upon exposure to a stimulus.

In another embodiment, the one or more entities comprise a biologically active entity, an inorganic material, or combinations thereof.

In a further embodiment, the biologically active entity is a drug, a protein, an antibody, an enzyme, a polynucleotide, or a particulate formulation thereof.

In a further embodiment, the inorganic material is a salt, a metal, a ceramic, an imaging agent, or a nanoparticulate formulation thereof.

In a further embodiment, the continuous outer shell phase defines an inner core phase comprising one or more entities which are retained inside the capsule upon exposure to the stimulus but interact with entities diffusing into the capsule following the application of the stimulus.

In a further embodiment, the entity retained inside the capsule is a sensing material and the entity diffusing into the capsule following exposure to the stimulus is the target of that sensing material.

In another embodiment, the stimulus is ultrasound, a magnetic field, irradiation, a pH change, a temperature change, or enzymatic activity.

In a further embodiment, the releasable cork phase is perturbed within the outer phase to create pores only during ultrasound activation. In another embodiment, after termination of the stimulus (for example, ultrasound), the pore is closed by re-integration of the cork phase.

The following non-limiting examples are illustrative of the present application:

EXAMPLES i. Synthesis of Materials of the Application

Synthesis and Conjugation of PLGA-Functionalized Corks

Poly(lactic acid-co-glycolic acid) (PLGA) surface functionalized corks: PLGA-coated corks were prepared similarly to the instructions of reference [47] in a two-step process. First, a portion of the hydroxyl surface groups of the SiO$_2$ corks were converted to amine groups. 4 g of SiO$_2$ microbeads (3 μm-10 μm diameter) were placed in a 500 mL Schlenk flask, suspended in 100 mL of toluene, and sonicated for 2 hours under nitrogen. Next, a solution of 10 mL of 3-aminopropyltriethoxysilane (henceforth abbreviated APTS) and 50 mL of anhydrous toluene was added dropwise to the 500 mL Schlenk flask under sonication and nitrogen and allowed to proceed for four hours. Following, the Schlenk flask was immersed in an oil bath and refluxed under nitrogen at 110° C. for 3 hours. After cooling to room temperature, the contents were vacuum filtered and placed in the thimble of a Soxhlet extractor, from which the unreacted small molecules were further extracted overnight at 120° C. The remaining solids content inside the Soxhlet thimble was dried in a vacuum oven for 24 hours to produce the aminated corks. Following, 1 g of aminated corks and 105 mg of 4-dimethylaminopyridine (DMAP) were dispersed in 20 mL of anhydrous N,N-dimethyl formamide (dry DMF) in a 100 mL Schlenk flask and sonicated for 2 hours under nitrogen.

Then, a solution of 600 mg of PLGA (40-75 kDa, 65:35 lactide:glycolide ratio) in 40 mL of dry DMF was added to the Schlenk flask and the reaction was further sonicated for 3 hours under nitrogen. Finally, a solution of 400 mg N-(3-dimethylaminopropyl)-N'-ethylcarbodiimide hydrochloride (EDC) in 40 mL of dry DMF was added to the reaction and sonicated under nitrogen for 2 hours to perform the grafting reaction. The Schlenk flask was then removed from the sonicator bath, refluxed under nitrogen for 6 hours at 160° C., and cooled, after which the product was purified through repeated centrifugation with DCM. The contents were dried in a vacuum oven at 36° C. for 24 h.

Synthesis of Fluorescently-Labeled Functionalized Corks

Fluorescent PLGA corks: For some imaging work, the PLGA corks were fluorescently labeled with fluorescein isothiocyanate (FITC) by dispersing PLGA corks in ethanol and excess FITC and stirring overnight in darkness at room temperature. The reacted resultant product was centrifuged at 3000 RPM, after which the supernatant was removed and replaced with clean ethanol. This purification process was repeated until the supernatant was clear and then twice more to ensure complete removal of non-bound fluorophore.

Characterization of Functionalized Corks

Figure 1:
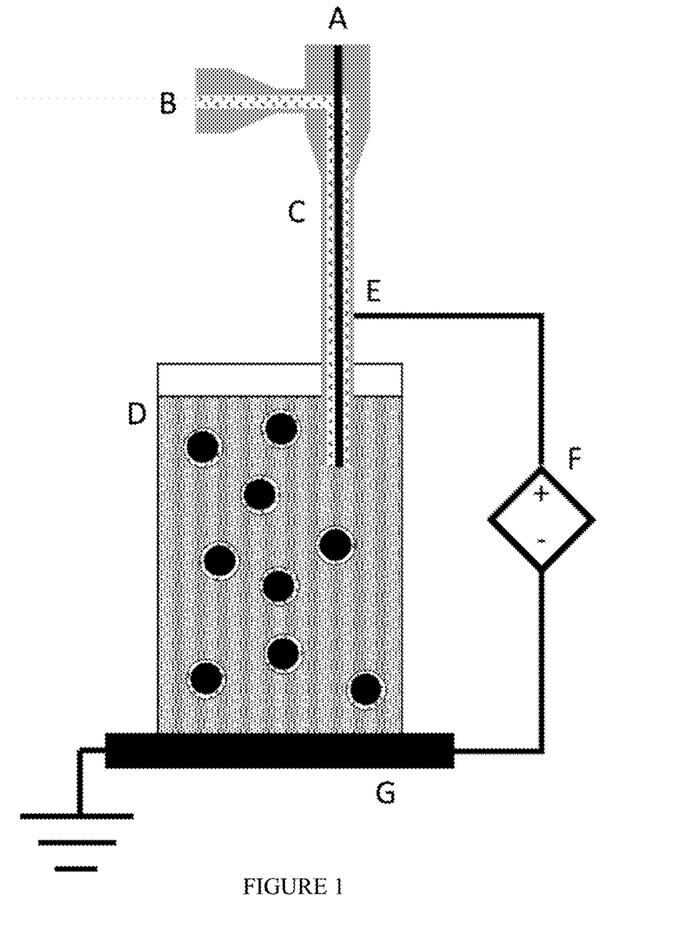
FIG. 1 shows an exemplary fabrication strategy used to create the exemplary capsules of the application.

Attenuated Total Reflectance Fourier Transform Infrared Spectroscopy (ATR-FTIR) was performed to track the efficacy of the PLGA conjugation reactions using 64 scans at a spectral resolution of 1 $cm^{-1}$.

ii. Fabrication of Delivery Vehicles of the Application Immersion Coaxial Electrospraying or Electrically-Assisted Interfacial Precipitation The apparatus used to fabricate the cork-shell capsules is illustrated in FIG. 1, where (A) is the liquid feed of the inner (aqueous) core that contains the dissolved payload and surfactant(s) necessary for stabilization; (B) is the liquid feed of the shell phase dissolved in a solvent that can also disperse the corks; (C) is the coaxial needle into which the core and shell phases are fed; (D) is the continuous phase into which the fabricated core-shell vehicles are extruded; (E) is the positive end of the high voltage generator which is attached to (C); (F) is the high voltage generator; and (G) is the grounding plate on which the collection bath is placed. Note that, in an embodiment, the contents of the inner core needle and the shell needle do not mix until they are introduced to each other the common terminal exit of the needle.

The base vehicle was fabricated using the following parameters: A 3 mL plastic syringe was loaded with a solution of 2.5 w/v % of BSA and distilled deionized water (henceforth referred to as DDW) and attached to a Tygon tube via a plastic luer lock. A 5 mL glass syringe was loaded with a 1-5 w/v % solution of PLGA in dichloromethane, a solution also including 0-2.5 w/v % of suspended PLGA corks when desired, and connected to peroxide-cured silicone tubing with metallic quick connect tubing components. The syringes are then loaded onto two syringe pumps set to 0.1 mL/hr and 1 mL/hr for the inner and outer flow rates respectively, with the tubing at each outlet connected to the respective inner and outer terminals of a coaxial needle with an inside gauge of 22G and an outer gauge of 18G. The needle is fully submerged inside a continuous phase comprised of an aqueous solution of 30 mg of PVA in 185 mL of DDW in a 200 mL beaker maintained under 300 RPM magnetic stirring. The positive end of a high voltage generator is connected to the needle while the negative ground is attached to a metal circle placed in a glass petri dish, upon which the continuous phase beaker is placed. Both of the syringe pumps are then turned on simultaneously, and a voltage of 15-18 kV is immediately applied. After one hour, the high voltage generator is turned off and the collection beaker is moved to a different stir plate to continue stirring at 300 RPM for 30 minutes to allow any residual dichloromethane to evaporate and solidify the shell. The fabricated vehicles are then concentrated and purified via three centrifugation cycles against DDW.

Characterization of the Delivery Vehicles

The encapsulation efficiency was measured by taking the capsule suspension off the stir plate, allowing the capsules to settle (~1 min.), and collecting the supernatant to assess the remaining (non-encapsulated) probe fraction using a multi-well plate reader, relating fluorescence to concentration based on a calibration curve measured based on known standard fluorescein concentrations.

To assess the size distribution of the capsules, capsules were dispersed onto microscope slides and allowed to dry. The size of the capsules was studied by imaging the capsules under a microscope and using ImageJ software to analyze their size. For analysis, a microscope image was converted to an 8-bit type file and the outlines of the capsules were identified using the contrasting technique. Noise was removed, and clumped capsules were separated using Imagers watershed tool. The diameters reported represent the average and standard deviation of the size of n>30 capsules analyzed per formulation using this method.

Figure 2:
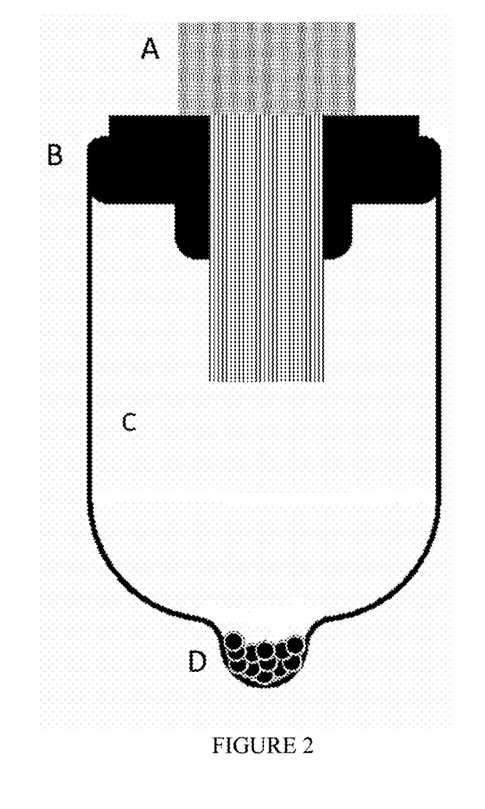
FIG. 2 shows a schematic of the geometry used for the ultrasound-triggered release studies in an exemplary embodiment of the application.

To assess the morphologies of the capsules, confocal microscopy was used to study both the internal and external component distributions within the vehicles. Two of the continuous shell material, core, and corks were fluorescently labeled with non-overlapping fluorophores in each imaging trial to correlate the distributions of different vehicle components. Rhodamine B (absorption 543 nm, emission 565 nm) was dissolved into the shell phase solution at a concentration of 0.001 w/v % to enable visualization of the shell and shell thickness in cases where the core and continuous phase are both water (in which Rhodamine B has low solubility). To visualize the core, fluorescein sodium salt (0.005 w/v %), FITC (0.001 w/v %), or Rhodamine 123 (0.001 w/v %) was dissolved into the core phase. To visualize the corks, the corks were further labeled with FITC by stirring the corks with FITC in ethanol overnight and then filtering via centrifugation [48]. Once the vehicles were prepared, they were deposited onto microscope slides and imaged using a 495 nm laser for FITC/Rhodamine 123 activation and a 546 nm laser for Rhodamine B activation. Images were taken at depths correlating to the size of the delivery vehicles. The images from the two fluorescent channels were superimposed and stacked to enable visualization in an orthogonal view or via a 3D map.

iii. Ultrasound Triggered Release Dynamics of the Delivery Vehicles of the Application Ultrasound Triggered Release Experiments An ultrasound generator with a frequency range of 0.1-20 MHz, a pulse voltage range of 100-400 V, and a pulse repetition frequency (PRF) of 0.1-5 kHz was used. A 3.5 MHz transducer was attached to the generator, and the transducer frequency was set to 3.5 MHz, the pulser voltage was set to 400 V, and the PRF was set to 5 kHz. A release chamber was fabricated and shown in FIG. 2, where (A) is an ultrasound probe, (B) is a plastic cylinder used to hold the sample as well as the ultrasound probe, (C) is a latex sample holder, and (D) is the dispersed capsules at the tip of the latex sample holder. In detail, a cylindrical piece of poly (vinyl chloride) (PVC) of thickness ~1 inch was hollowed out in the center to fit the diameter of the ultrasound transducer, and an additional hole was made eccentrically in the PVC to fit a 1000 µL pipette tip. The ultrasound transducer was then placed and secured in the central hole of the PVC such that the face of the transducer was exposed beyond the thickness of the PVC cylinder. A thin latex sample holder was attached onto the PVC cylinder to enable the sample-to-probe distance to be controlled from 2 cm to 10 cm. An 8 L water bath of cubic dimensions 8.25×8.25× 8.25 inches was heated to 37° C. to simulate physiological conditions. A cover was placed on top with a hole cut in its center to fit the PVC cylinder that holds the capsules in the latex sample holder and the ultrasound transducer.

Ultrasound-Triggered Release Kinetics of Delivery Vehicles

All capsules fabricated by a single ImCES fabrication cycle were placed at the tip of the latex sample holder described in [0094], with the rest of the sample holder filled with DDW to a total volume of 40 mL. The ultrasound transducer was placed in the central hole and secured, after which all air bubbles were removed from the system using an air escape hole. Triplicate 200 µL samples were collected from the top of the sample holder chamber before any ultrasonication was started to account for any potential initial burst release. The ultrasound was then turned on for a time period ranging from 5 minutes to 1 hour, with triplicate 200 µL samples taken at various time points. When the ultrasound was not being used, the probe was removed and the cylinder was placed inside an incubator maintained at 37° C. Aliquots were taken at various times while the samples were in the incubator. The samples were dispensed into a 96-well plate, and DDW was replaced to normalize the volume inside the sample holder after each sampling period. Following, the concentration of the fluorescent payload was measured using a multiwell plate reader using an absorption wavelength of 485 nm and emission wavelength of 535 nm, with each measured value normalized for the fluorescence (if any) measured immediately before the ultrasound pulse was applied.

Investigation of Ultrasound Release Mechanism

To assess the modality of pore formation (whether dynamic or permanent), the cork and shell phases are fluorescently labeled and subjected to ultrasound for triggered release. After this, 3×1 mL aliquots are taken from the tip of the latex sample holder and vacuum filtered using a 25 µm filter that retains the intact capsules but allows any released corks or released payloads to pass through. The filter is washed using 10 mL of DDW, after which the filtrate is collected and centrifuged at 600 RPM for 5 minutes. An aliquot containing the pellet is removed and imaged on a confocal microscope to confirm the presence of fluorescently labelled corks and/or payload.

Figure 3:
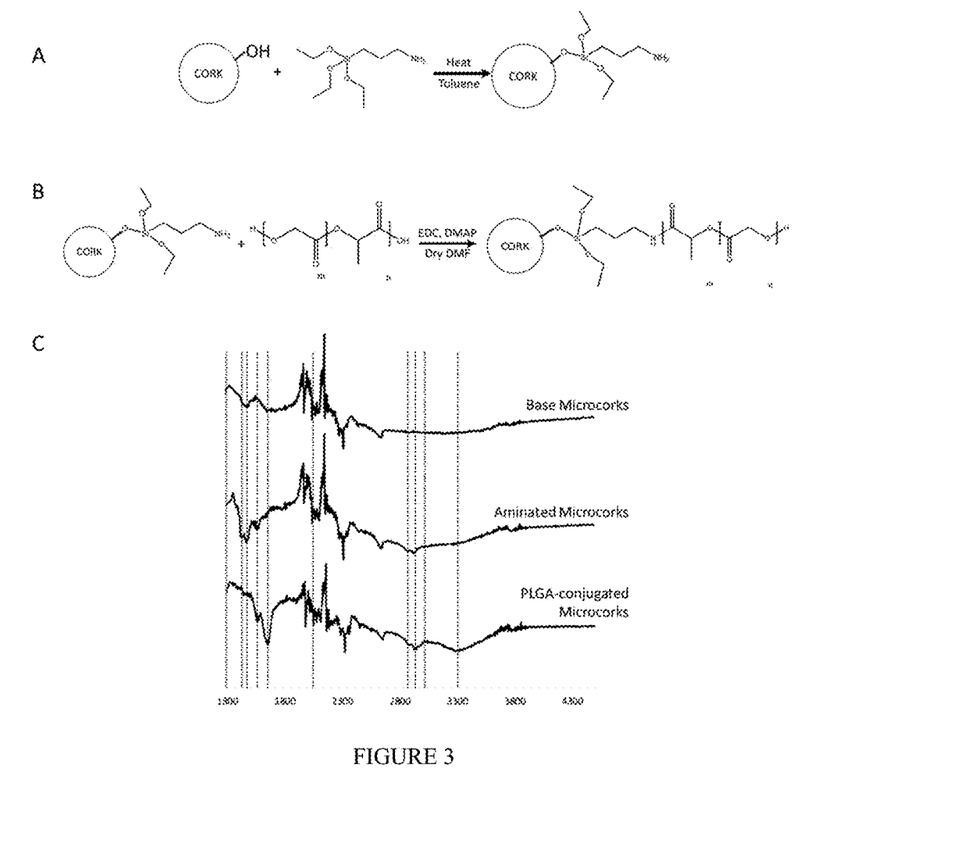
FIG. 3 shows the reaction mechanisms associated with the conjugation of PLGA to the corks and infrared spectroscopy evidence of cork functionalization in exemplary embodiments of the application.

Example 1: Fluorescein Sodium Salt Release Studies Comparing Corked Delivery Vehicles Vs Uncorked Delivery Vehicles While not essential to the functionality of the vehicles, in an embodiment, the surface of the corks is functionalized with the same polymer to form the capsule (PLGA) to enhance the dispersibility of corks in the shell. FIG. 3 shows the process of cork functionalization with PLGA, with FIG. 3A showing the mechanism used to aminate the corks (MC) by functionalizing the hydroxide termini of the PLGA chains with 3-aminopropyltriethoxysilane (APS) and FIG. 3B showing the subsequent carbodiimide-mediated conjugation reaction to functionalize those amine termini with carboxylic acid groups of carboxy-terminated PLGA to yield PLGA-conjugated corks. Comparing the ATR-FTIR spectra of the unmodified corks with the aminated corks, a broad peak appears between 1600 $cm^{-1}$ and 1900 $cm^{-1}$ ($NH_2$ bending) and two shallow peaks appear at 2825 $cm^{-1}$ and 2875 $cm^{-1}$ (CH bond vibration of APS) (FIG. 3C), confirming successful amination; subsequently, upon PLGA conjugation, a sharp peak appears at 1650 $cm^{-1}$ corresponding to the C=O stretch of the ester linkages in the polyester and a broad peak is observed between 2950 $cm^{-1}$ and 3000 $cm^{-1}$ corresponding to the $CH_2$ and $CH_3$ groups from PLGA (FIG. 3C).

Figure 4:
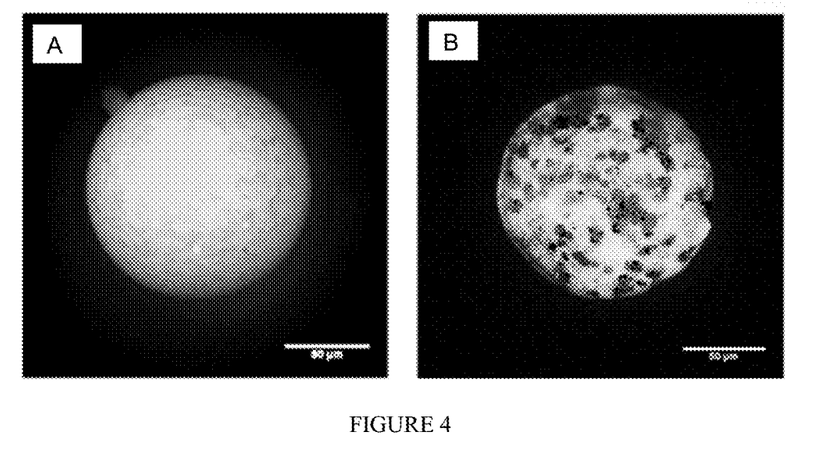
FIG. 4 shows fluorescence images comparing the structure of a hollow shell particle fabricated without and with corks in exemplary embodiments of the application.

To compare release profiles achieved with and without corks and with and without ultrasound activation, non-corked (conventional core-shell) capsules were fabricated with a core phase comprised of 10 w/v % BSA and 0.5 w/w % of fluorescein sodium salt (relative to BSA) in DDW (extruded at 0.3 mL/h), a shell phase comprised of 5 w/v % PLGA in dichloromethane (extruded at 3 mL/h), and a continuous phase comprised of 30 mg PVA in 185 mL DDW stirred at 300 RPM. A voltage of 18 kV was used for particle formation. Corked vehicles were fabricated using the same parameters but with the inclusion of a 2.5 w/v % dispersion of PLGA-functionalized corks in the shell phase. 3 fabrication cycles were performed for each of the corked and uncorked delivery vehicles to confirm reproducibility. Cork encapsulation within the shell is confirmed by fluorescence microscopy of a rhodamine-labeled shell in the presence of unlabeled corks (FIG. 4). In the absence of corks, the entire shell fluoresces (FIG. 4A); when corks are included in the fabrication process, dark spots corresponding to the approximate cork diameters are observed in the shell phase (FIG. 4B) confirming cork encapsulation within the shell.

Figure 5:
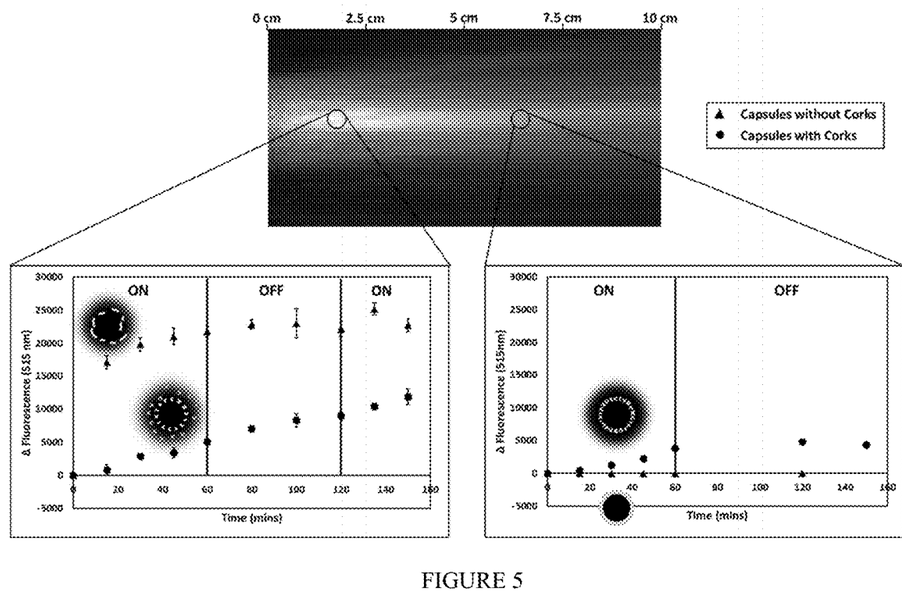
FIG. 5 shows release kinetics of fluorescein from capsules with and without corks as a function of ultrasound exposure time and intensity in exemplary embodiments of the application.
Figure 6:
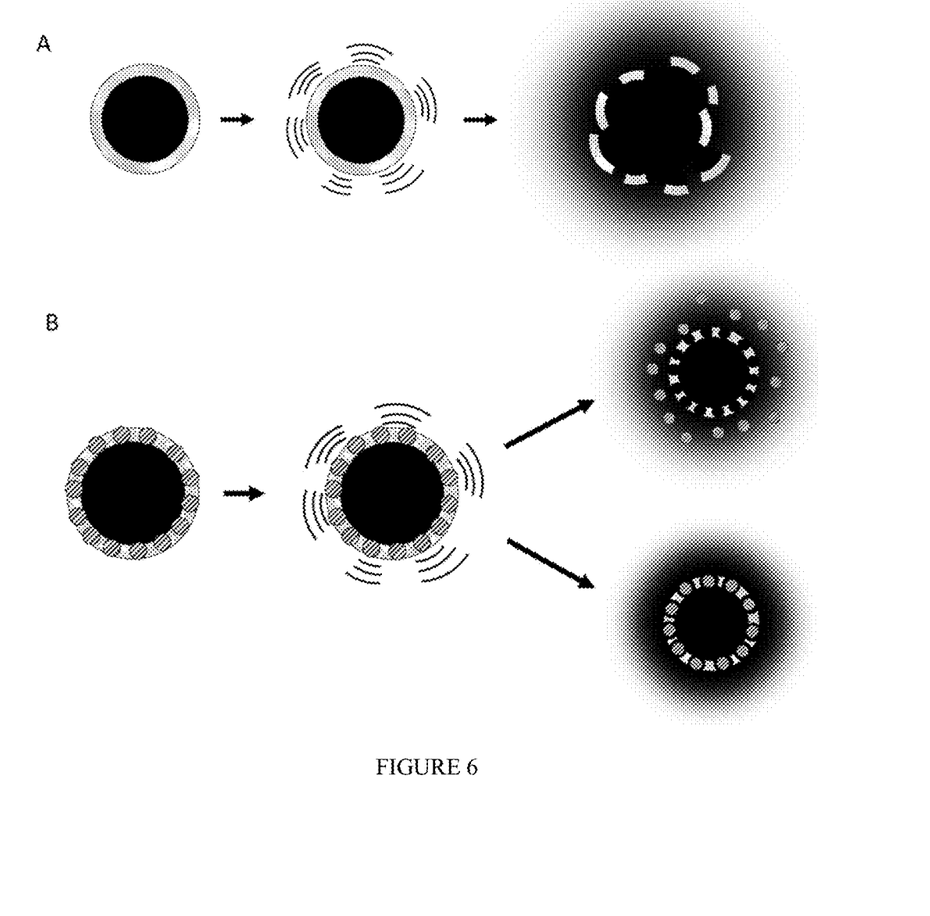
FIG. 6 shows mechanisms associated with ultrasound triggered drug delivery using exemplary materials of the application.
Figure 7:
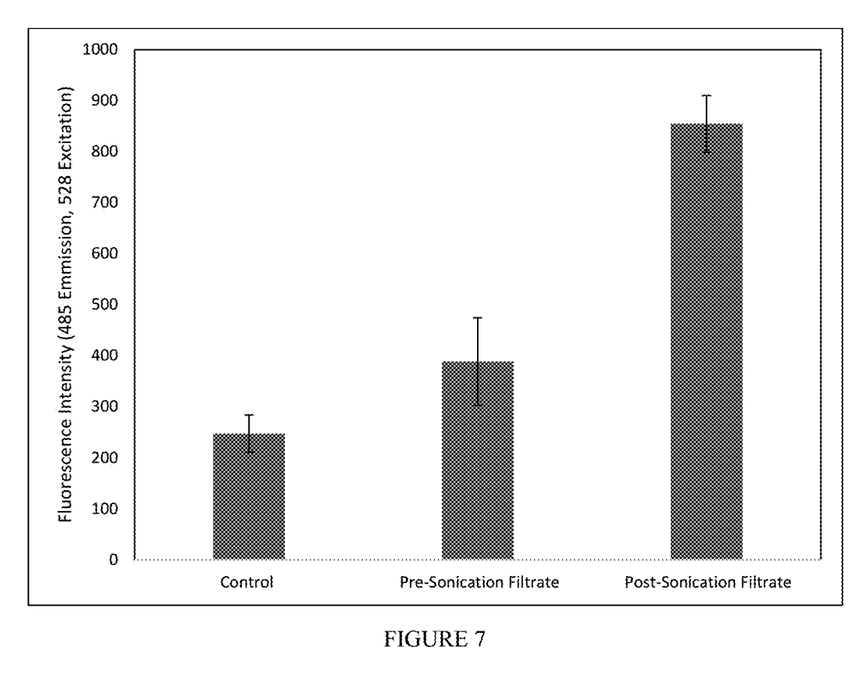
FIG. 7 shows release kinetics of fluorescein-labelled corks from the capsules with and without ultrasound exposure using exemplary materials of the application.

FIG. 5 shows the release kinetics of fluorescein sodium salt from both corked and uncorked fluorescein sodium salt-loaded capsules when exposed to a 1 hour ultrasound pulse at different distances (2 cm or 6.5 cm) away from the ultrasound transducer followed by 1 hour of no ultrasound exposure. The contour plot at the top of FIG. 5 is a raster scan of the measured intensity of the local ultrasound power applied by the ultrasound transducer at each position within the release apparatus, with white zones representing higher acoustic pressures and black zones representing lower acoustic pressures. The release profiles shown in the graphs in FIG. 5 are discussed in conjunction with FIG. 6, which shows the potential release mechanisms associated with ultrasound activation of the corks. When the capsules are placed 2 cm away from the transducer (a position of higher acoustic pressure), a very fast release of fluorescein is observed associated with burst release or UTMD for the capsules without corks (FIG. 6A); when corks are included in the shell, vehicles release at a constant rate during ultrasound exposure and a slowed but still significant release in the absence of ultrasound exposure (FIG. 5—left graph). Without wishing to be bound by theory, this result for the capsules with corks suggests that at least some fraction of corks is popped out of the shell without fracturing the shell (FIG. 6B—top), avoiding the burst release associated with UTMD while preserving continuous delivery even when the ultrasound stimulus is removed. FIG. 7 confirms that the corks are popped out in such situations, with a significant concentration of FITC-labeled corks detected in the filtrate (in which the pore size is too small for the whole vehicles to pass through) following ultrasound exposure but no significant increase in fluorescence is observed relative to the background signal in the absence of ultrasound. In contrast, when capsules are placed 6.5 cm away from the transducer (a position of lower acoustic pressure), no release was observed from capsules prepared without corks while a pulsatile release was observed from corked capsules, with the release proceeding with zero-order kinetics while ultrasound was applied but effectively stopping in the absence of ultrasound (FIG. 5—right graph). Again without wishing to be bound by theory, this result is consistent with the corks being vibrated within the shell to transiently create free volume to permit drug release without being popped out of the shell entirely (in which case release would continue in the "off" state) (FIG. 6B—bottom). As such, depending on the ultrasound power applied, the corked capsules described in this application can enable continuous controlled release activated at a particular time by an ultrasound pulse (higher ultrasound powers, corks pop out) or pulsatile release in which controlled release is achieved only when the ultrasound stimulus is applied (lower ultrasound powers, corks vibrate but remain in the shell).

While the present application has been described with reference to examples, it is to be understood that the scope of the claims should not be limited by the embodiments set forth in the examples, but should be given the broadest interpretation consistent with the description as a whole.

Other features and advantages of the present application will become apparent from the following detailed description. It should be understood, however, that the detailed description and the specific examples, while indicating embodiments of the application, are given by way of illustration only and the scope of the claims should not be limited by these embodiments but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE APPLICATION

1. Caruso, M. M., et al., *Mechanically-induced chemical changes in polymeric materials*. Chem Rev, 2009. 109(11): p. 5755-98.
2. Coussios, C. C. and R. A. Roy, *Applications of Acoustics and Cavitation to Noninvasive Therapy and Drug Delivery*. Annu Rev Fluid Mech, 2008. 40(1): p. 395-420.
3. Escoffre, J. M., et al., *Doxorubicin delivery into tumor cells with ultrasound and microbubbles*. Mol Pharm, 2011. 8(3): p. 799-806.
4. Liu, J., et al., *pH-sensitive nano-systems for drug delivery in cancer therapy*. Biotechnol Adv, 2014. 32(4): p. 693-710.
5. Li, J., C. Nagamani, and J. S. Moore, *Polymer mechanochemistry: from destructive to productive*. Acc Chem Res, 2015. 48(8): p. 2181-90.
6. Choi, S. W., Y. Zhang, and Y. Xia, *A temperature-sensitive drug release system based on phase-change materials*. Angew Chem Int Ed Engl, 2010. 49(43): p. 7904-8.
7. Hoare, T. and R. Pelton, *Highly pH and Temperature Responsive Microgels Functionalized with Vinylacetic Acid*. Macromolecules, 2004. 37(7): p. 2544-2550.
8. Li, W., et al., *Gold nanocages covered with thermally-responsive polymers for controlled release by high-intensity focused ultrasound*. Nanoscale, 2011. 3(4): p. 1724-30.
9. Liu, H., et al., *Hydrophobic interaction-mediated capture and release of cancer cells on thermoresponsive nanostructured surfaces*. Adv Mater, 2013. 25(6): p. 922-7.
10. Ta, T. and T. M. Porter, *Thermosensitive liposomes for localized delivery and triggered release of chemotherapy*. J Control Release, 2013. 169(1-2): p. 112-25.
11. Tan, H., et al., *Thermosensitive injectable hyaluronic acid hydrogel for adipose tissue engineering*. Biomaterials, 2009. 30(36): p. 6844-53.
12. Cheng, W., et al., *pH-Sensitive Delivery Vehicle Based on Folic Acid-Conjugated Polydopamine-Modified Mesoporous Silica Nanoparticles for Targeted Cancer Therapy*. ACS Appl Mater Interfaces, 2017. 9(22): p. 18462-18473.
13. Felber, A. E., M. H. Dufresne, and J. C. Leroux, *pH-sensitive vesicles, polymeric micelles, and nanospheres prepared with polycarboxylates*. Adv Drug Deliv Rev, 2012. 64(11): p. 979-92.
14. Li, H. J., et al., *Smart Superstructures with Ultrahigh pH-Sensitivity for Targeting Acidic Tumor Microenvironment: Instantaneous Size Switching and Improved Tumor Penetration*. ACS Nano, 2016. 10(7): p. 6753-61.
15. Hu, J., G. Zhang, and S. Liu, *Enzyme-responsive polymeric assemblies, nanoparticles and hydrogels*. Chem Soc Rev, 2012. 41(18): p. 5933-49.
16. Li, Y., et al., *Enzyme-Responsive Polymeric Vesicles for Bacterial-Strain-Selective Delivery of Antimicrobial Agents*. Angew Chem Int Ed Engl, 2016. 55(5): p. 1760-4.
17. Muanprasat, C. and V. Chatsudthipong, *Chitosan oligosaccharide: Biological activities and potential therapeutic applications*. Pharmacol Ther, 2017. 170: p. 80-97.
18. Napoli, A., et al., *Glucose-oxidase Based Self-Destructing Polymeric Vesicles*. Langmuir, 2004. 20(9): p. 3487-3491.
19. Yu, J., et al., *Stimuli-Responsive Delivery of Therapeutics for Diabetes Treatment*. Bioeng Transl Med, 2016. 1(3): p. 323-337.
20. Di, J., et al., *Ultrasound-triggered noninvasive regulation of blood glucose levels using microgels integrated with insulin nanocapsules*. Nano Research, 2017. 10(4): p. 1393-1402.
21. Song, G., et al., *Perfluorocarbon-Loaded Hollow Bi2Se3 Nanoparticles for Timely Supply of Oxygen under Near-Infrared Light to Enhance the Radiotherapy of Cancer*. Adv Mater, 2016. 28(14): p. 2716-23.
22. Volodkin, D. V., A. G. Skirtach, and H. Mohwald, *Near-IR remote release from assemblies of liposomes and nanoparticles*. Angew Chem Int Ed Engl, 2009. 48(10): p. 1807-9.
23. Xu, J. S., et al., *Synthesizing and binding dual-mode poly (lactic-co-glycolic acid) (PLGA) nanobubbles for cancer targeting and imaging*. Biomaterials, 2010. 31(7): p. 1716-22.
24. Brazel, C. S., *Magnetothermally-responsive nanomaterials: combining magnetic nanostructures and thermally-sensitive polymers for triggered drug release*. Pharm Res, 2009. 26(3): p. 644-56.
25. Ulbrich, K., et al., *Targeted Drug Delivery with Polymers and Magnetic Nanoparticles: Covalent and Noncovalent Approaches, Release Control, and Clinical Studies*. Chem Rev, 2016. 116(9): p. 5338-431.
26. Zhang, Y., et al., *Mechanical Force-Triggered Drug Delivery*. Chem Rev, 2016. 116(19): p. 12536-12563.
27. Figueiredo, M. and R. Esenaliev, *PLGA Nanoparticles for Ultrasound-Mediated Gene Delivery to Solid Tumors*. J Drug Deliv, 2012. 2012: p. 767839.

28. Hernot, S. and A. L. Klibanov, *Microbubbles in ultrasound-triggered drug and gene delivery*. Adv Drug Deliv Rev, 2008. 60(10): p. 1153-66.
29. Li, P., et al., *Ultrasound triggered drug release from 10-hydroxycamptothecin-loaded phospholipid microbubbles for targeted tumor therapy in mice*. J Control Release, 2012. 162(2): p. 349-54.
30. Deckers, R., et al., *New insights into the HIFU-triggered release from polymeric micelles*. Langmuir, 2013. 29(30): p. 9483-90.
31. Prince, J. L. and J. M. Links, *Medical Imaging Signals and Systems, in Medical Imaging Signals and Systems*. 2006, Pearson Prentice Hall.
32. Moyer, L. C., et al., *High-intensity focused ultrasound ablation enhancement in vivo via phase-shift nanodroplets compared to microbubbles*. J Ther Ultrasound, 2015. 3: p. 7.
33. Liu, Y., H. Miyoshi, and M. Nakamura, *Encapsulated ultrasound microbubbles: therapeutic application in drug/gene delivery*. J Control Release, 2006. 114(1): p. 89-99.
34. Villanueva, F. S., *Ultrasound mediated destruction of DNA-loaded microbubbles for enhancement of cell-based therapies: new promise amidst a confluence of uncertainties?* JACC Cardiovasc Imaging, 2009. 2(7): p. 880-2.
35. Fong, W. K., et al., *Responsive self-assembled nanostructured lipid systems for drug delivery and diagnostics*. J Colloid Interface Sci, 2016. 484: p. 320-339.
36. Kang, M., G. Huang, and C. Leal, *Role of lipid polymorphism in acoustically sensitive liposomes*. Soft Matter, 2014. 10(44): p. 8846-54.
37. Schroeder, A., et al., *Controlling Liposomal Drug Release with Low Frequency Ultrasound: Mechanism and Feasibility*. Langmuir, 2007. 23(7): p. 4019-4025.
38. Tang, J., et al., *Controlled drug release from ultrasound-visualized elastic eccentric microcapsules using different resonant modes*. J Mater Chem B, 2018. 6(13): p. 1920-1929.
39. Swider, E., et al., *Customizing poly(lactic-co-glycolic acid) particles for biomedical applications*. Acta Biomater, 2018. 73: p. 38-51.
40. Ahmad, Z., et al., *Generation of multilayered structures for biomedical applications using a novel tri-needle coaxial device and electrohydrodynamic flow*. J R Soc Interface, 2008. 5(27): p. 1255-61.
41. Gao, Y., et al., *Optimising the shell thickness-to-radius ratio for the fabrication of oil-encapsulated polymeric microspheres*. Chem Eng J, 2016. 284: p. 963-971.
42. Jaworek, A. and A. T. Sobczyk, *Electrospraying route to nanotechnology: An overview*. J Electrostat, 2008. 66(3-4): p. 197-219.
43. Li, Z. and C. Wang, *Effects of Working Parameters on Electrospinning*, in *One-Dimensional nanostructures*. 2013. p. 15-28.
44. Moghaddam, M. K., S. M. Mortazavi, and T. Khaymian, *Micro/nano-encapsulation of a phase change material by coaxial electrospray method*. Iran Polym J, 2015. 24(9): p. 759-774.
45. Smallwood, I. M., *Handbook of Organic Solvent Properties*. 1996, New York: Halsted Press.
46. Xu, Y. and M. A. Hanna, *Electrospray encapsulation of water-soluble protein with polylactide. Effects of formulations on morphology, encapsulation efficiency and release profile of particles*. Int J Pharm, 2006. 320(1-2): p. 30-6.
47. Wu, F., et al., *Grafting polymerization of polylactic acid on the surface of nano-$SiO_2$ and properties of PLA/PLA-grafted-$SiO_2$ nanocomposites*. J Appl Polym Sci, 2013. 129(5): p. 3019-3027.
48. Lee, Y.-C., et al., *Optical Properties of Fluorescein labeled Organoclay*. Photochem Photobiol, 2010. 86(3): p. 520-527.

The invention claimed is:

1. A core-shell particle, comprising
   1) An outer shell comprising at least one first polymer; and
   2) at least one particulate phase embedded and/or dispersed within the outer shell, wherein the particulate phase comprises at least one inorganic oxide, metal salt, polymer, organometallic compound or contrast agent, and wherein the at least one particulate phase is releasable from or perdurable within the outer shell to create a pore in the outer shell upon exposure to an external stimulus, and wherein the at least one particulate phase has a different mechanical index from the outer shell.

2. The core-shell particle of claim 1, wherein the at least one particulate phase is irreversibly released from the outer shell.

3. The core-shell particle of claim 1, wherein the at least one particulate phase is transiently perturbed within the outer shell.

4. The core-shell particle of claim 1, wherein the polymer of the shell is a polyester, a polyurethane, a poly(meth)acrylate, a poly(amino ester), a polyanhydride, a polyimide, a polyurea, a polyolefin, or copolymers thereof.

5. The core-shell particle of claim 4, wherein the polymer of the shell is a polyester.

6. The core-shell particle of claim 5, wherein the polyester is poly(lactic acid-co-glycolic acid).

7. The core-shell particle of claim 6, wherein the poly(lactic acid-co-glycolic acid) has the formula wherein m and n are integers from 1 to 10,000.

8. The core-shell particle of claim 1, wherein the at least one particulate phase comprises an inorganic oxide.

9. The core-shell particle of claim 8, wherein the inorganic oxide is silicon dioxide, sodium oxide, calcium oxide, potassium oxide, barium oxide, or mesoporous silica, or mixtures thereof.

10. The core-shell particle of claim 9, wherein the inorganic oxide is silicon dioxide.

11. The core-shell particle of claim 1, wherein the at least one particulate phase comprises an inorganic oxide covalently linked to a second polymer.

12. The core-shell particle of claim 11, wherein the silicon dioxide is covalently linked to the second polymer with an amine linker.

13. The core-shell particle of claim 12, wherein the second polymer is a polyester, a polyurethane, a poly(meth)acrylate, a poly(amino ester), a polyurea, a polyolefin, or copolymers thereof.

14. The core-shell particle of claim 13, wherein the polyester is poly(lactic acid-co-glycolic acid).

15. The core-shell particle of claim 14, wherein the poly(lactic acid-co-glycolic acid) has the formula wherein m and n are integers from 1 to 10,000.

16. The core-shell particle of claim 1, wherein the at least one particulate phase has the following formula wherein m and n are integers from 1 to 10,000.

17. The core-shell particle of claim 1, wherein the outer shell defines an inner core comprising one or more materials which are released from the inner core upon exposure to the stimulus.

18. The core-shell particle of claim 17, wherein the one or more materials comprise a biologically active entity, an inorganic material, or combinations thereof.

19. The core-shell particle of claim 18, wherein the biologically active entity is a drug, a protein, an antibody, an enzyme, a polynucleotide, or a particulate, complex, or conjugate formulation thereof.

20. The core-shell particle of claim 18, wherein the inorganic material is a salt, a metal, a ceramic, an imaging agent, or a particulate, complex, or conjugate formulation thereof.

21. The core-shell particle of claim 1, wherein the stimulus is ultrasound, a magnetic field, irradiation, a pH change, a temperature change, or enzymatic activity.

22. The core-shell particle of claim 17, wherein the release or perturbation of the at least one particulate phase within the outer shell upon exposure to an external stimulus mediates the transport of one or more entities into the inner core.

23. The core-shell particle of claim 22 in which one or more entities transporting into the inner core are analytes for an encapsulated sensor.

* * * * *

UNITED STATES PATENT AND TRADEMARK OFFICE
CERTIFICATE OF CORRECTION

| | |
|---|---|
| PATENT NO. | : 11,883,540 B2 |
| APPLICATION NO. | : 17/320446 |
| DATED | : January 30, 2024 |
| INVENTOR(S) | : Todd Hoare et al. |

It is certified that error appears in the above-identified patent and that said Letters Patent is hereby corrected as shown below:

In the Claims

Column 18, Line 18 Claim 1, amend the word "perdurable" to "perturable".

Signed and Sealed this
Twenty-eighth Day of May, 2024

Katherine Kelly Vidal
*Director of the United States Patent and Trademark Office*